US00PP13943P29

(12) United States Plant Patent
Trees

(10) Patent No.: US PP13,943 P2
(45) Date of Patent: Jul. 8, 2003

(54) VERBENA PLANT NAMED 'BALAZWHIT'

(75) Inventor: Scott C. Trees, Shell Beach, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/114,450

(22) Filed: Apr. 1, 2002

(51) Int. Cl.[7] ..... A01H 5/00
(52) U.S. Cl. ..... Plt./308
(58) Field of Search ..... Plt./308

*Primary Examiner*—Kent Bell
(74) *Attorney, Agent, or Firm*—C. A. Whealy

(57) ABSTRACT

A new and distinct cultivar of Verbena plant named 'Balazwhit', characterized by its compact, mounded and outwardly spreading plant habit; dark green leaves; and white-colored flowers.

1 Drawing Sheet

BOTANICAL CLASSIFICATION/CULTIVAR DESIGNATION

*Verbena hybria* cultivar 'Balazwhit'.

BACKGROUND OF THE INVENTION

The present Invention relates to a new and distinct cultivar of Verbena plant, botanically known as *Verbena hybrida*, and hereinafter referred to by the name 'Balazwhit'.

The new Verbena is a product of a planned breeding program conducted by the Inventor in Arroyo Grande, Calif. The objective of the breeding program is to develop new freely flowering Verbena cultivars with an outwardly spreading growth habit and attractive leaf and flower coloration.

The new Verbena originated from a cross-pollination made by the Inventor in 2000 of a proprietary *Verbena hybrida* selection identified as code number 236, not patented, as the female, or seed, parent with a proprietary *Verbena hybrida* selection identified as code name Verb-D, not patented, as the male, or pollen, parent. The cultivar Balazwhit was discovered and selected by the Inventor as a flowering plant within the progeny from this cross-pollination in a controlled environment in Arroyo Grande, Calif.

Asexual reproduction of the new cultivar by cuttings taken at Arroyo Grande, Calif., since February, 2000, has shown that the unique features of this new Verbena are stable and reproduced true to type in successive generations of asexual reproduction.

SUMMARY OF THE INVENTION

The following traits have been repeatedly observed and are determined to be the unique characteristics of 'Balazwhit'. These characteristics in combination distinguish 'Balazwhit' as a new and distinct cultivar:

1. Compact, mounded and outwardly spreading plant habit.

2. Dark green leaves.

3. White-colored flowers.

Plants of the new Verbena differ primarily from plants of the parent selections in growth habit and leaf shape.

The new Verbena can be compared to the cultivar, 'Sunmariho', disclosed in U.S. Plant Pat. No. 10,743.

However, in side-by-side comparisons conducted in West Chicago, Ill., plants of the new Verbena differed from plants of the cultivar Sunmariho in the following characteristics:

1. Plants of the new Verbena were more compact and not as vigorous as plants of the cultivar Sunmariho.

2. Plants of the new Verbena had smaller leaves than plants of the cultivar Sunmariho.

3. Flower color of plants of the new Verbena was white whereas flower color of plants of the cultivar Sunmariho was creamy white.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of multiple flowering plants of 'Balazwhit' grown in a container. Flower and foliage colors in the photograph differ slightly from the color values cited in the detailed botanical description which accurately describe the colors of the new Verbena.

DETAILED BOTANICAL DESCRIPTION

The cultivar Balazwhit has not been observed under all possible environmental conditions. The phenotype may vary somewhat with variations in environment such as temperature and light intensity, without, however, any variance in genotype. The aforementioned photograph and following observations and measurements describe plants grown in West Chicago, Ill., under commercial practice in a polycarbonate-covered greenhouse with day temperatures about 20 to 22° C., night temperatures about 18 to 20° C. and light levels about 5,000 to 7,500 foot-candles. Plants used for the photograph and description were about six weeks from planting rooted cuttings. In the following description, color references are made to The Royal Horticultural Society Colour Chart, 1995 Edition, except where general terms of ordinary dictionary significance are used.

Botanical classification: *Verbena hybrida* cultivar Balazwhit.

Parentage:

*Female parent.*—Proprietary *Verbena hybrida* selection identified as code number 236, not patented.

*Male parent.*—Proprietary *Verbena hybrida* selection identified as code name Verb-D, not patented.

Propagation:

*Type cutting.*—Stem cuttings.

*Time to initiate roots.*—About 7 days at 18° C.

*Time to develop roots.*—About 21 days at 18° C.

*Root description.*—Fine, fibrous, white in color.

*Rooting habit.*—Freely branching.

Plant description:

*General appearance.*—Compact, mounded and outwardly spreading plant habit; eventually trailing. Appropriate for 10-cm and larger containers.

*Growth and branching habit.*—Freely basal branching, dense and bushy growth. Pinching, that is, removal of the terminal apices, enhances branching with lateral branches potentially forming at every node. Moderately vigorous.

*Plant height.*—About 10 cm.

*Plant diameter or spread.*—About 45.4 cm.

*Lateral branch description.*—Length: About 25 cm. Diameter: About 2 mm. Internode length: About 4.5 cm. Texture: Pubescent. Color: 144B.

*Foliage description.*—Arrangement: Opposite, simple. Length: About 3 cm. Width: About 2.1 cm. Shape: Ovate. Apex: Acute. Base: Attenuate. Margin: Lobed. Texture, upper and lower surfaces: Pubescent. Venation pattern: Pinnate. Color: Young and fully expanded foliage, upper surface: 137A; venation, 145C. Young and fully expanded foliage, lower surface: 137C; venation, 145C. Petiole: Length: About 6 mm. Diameter: About 2 mm. Texture, upper and lower surfaces: Pubescent. Color, upper and lower surfaces: 145C.

Flower description:

*Flower type and habit.*—Single upright salverform white-colored flowers arranged on hemispherical corymbs. Freely flowering with about 14 flower per corymb. Inflorescences positioned above and beyond the foliage. Flowers last about three to four days under greenhouse conditions. Flowers persistent. Flowers not fragrant.

*Flowering season.*—In the garden, flowering is continuous from spring until fall.

*Inflorescence height.*—About 4 cm.

*Inflorescence diameter.*—About 5.3 cm.

*Flower size.*—Diameter: About 2.1 cm. Tube length: About 2 cm. Throat diameter (at base): About 2 mm.

*Flower buds.*—Length: About 4 mm. Diameter: About 3 mm. Shape: Club-shaped. Color: 145D.

*Petals.*—Quantity/arrangement: Five per flower fused at base. Lobe length: About 9 mm. Lobe width: About 8 mm. Shape: Obovate. Apex: Rounded. Margin: Entire. Texture, upper and lower surfaces: Glabrous, smooth. Color: When opening and fully opened, upper surface: 155D; towards base, 145B to 145C. When opening and fully opened, lower surface: 155D. Throat: 145D. Tube: 145D.

*Sepals.*—Quantity/arrangement: Five, fused into a tube. Length: About 1.3 cm. Diameter: About 2 mm. Shape: Elongated. Apex: Acute. Margin: Entire. Texture, upper and lower surfaces: Pubescent. Color, upper and lower surfaces: 144A.

*Pedicels.*—Length: About 6.8 cm. Diameter: About 2 mm. Strength: Strong. Angle to stem: Acute. Texture: Pubescent. Color: 145C.

*Reproductive organs.*—Stamens: Quantity: Four per flower. Anther shape: Ovoid. Anther length: About 1 mm. Anther color: 145B. Pollen amount: Sparse. Pollen color: 6C. Pistils: Quantity: One per flower. Pistil length: About 1.9 cm. Stigma length: Less than 1 mm. Stigma shape: Bi-lobed. Stigma color: 144B. Style length: About 1.7 cm. Style color: 144C. Ovary diameter: About 2 mm. Ovary color: 144A.

*Seed/fruit.*—Seed and fruit production has not been observed.

Disease/pest resistance: Plants of the new Verbena have not been observed to be resistant to pathogens and pests common to Verbena.

Temperature tolerance: Plants of the new Verbena have been observed to be tolerant to temperatures ranging from 2 to 40° C.

It is claimed:

1. A new and distinct cultivar of Verbena plant named 'Balazwhit', as illustrated and described.

* * * * *

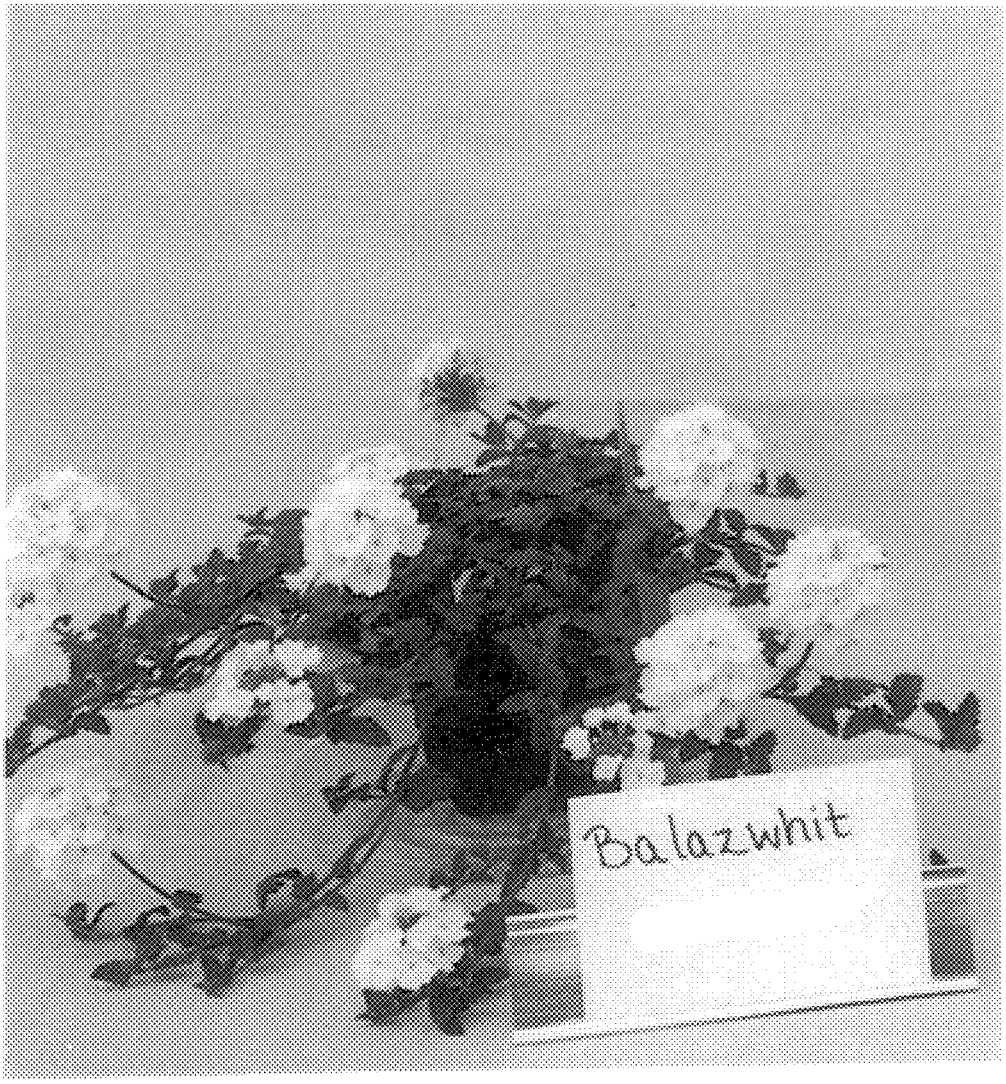
Balazwhit